United States Patent
Matsuoka et al.

(10) Patent No.: US 9,845,719 B2
(45) Date of Patent: Dec. 19, 2017

(54) GAS SENSOR CONTROL DEVICE

(71) Applicant: DENSO CORPORATION, Kariya, Aichi-pref. (JP)

(72) Inventors: Mikiyasu Matsuoka, Kariya (JP); Yasuo Mukai, Kariya (JP); Shingo Nakata, Kariya (JP); Yuji Yamada, Kariya (JP)

(73) Assignee: DENSO CORPORATION, Kariya (JP)

( * ) Notice: Subject to any disclaimer, the term of this patent is extended or adjusted under 35 U.S.C. 154(b) by 86 days.

(21) Appl. No.: 14/910,781

(22) PCT Filed: Jul. 31, 2014

(86) PCT No.: PCT/JP2014/004014
§ 371 (c)(1),
(2) Date: Feb. 8, 2016

(87) PCT Pub. No.: WO2015/019583
PCT Pub. Date: Feb. 12, 2015

(65) Prior Publication Data
US 2016/0201540 A1    Jul. 14, 2016

(30) Foreign Application Priority Data
Aug. 9, 2013   (JP) ................................ 2013-167128

(51) Int. Cl.
*F01N 11/00*   (2006.01)
*G01N 27/406*   (2006.01)
(Continued)

(52) U.S. Cl.
CPC .......... *F01N 11/007* (2013.01); *F01N 11/002* (2013.01); *F01N 13/008* (2013.01);
(Continued)

(58) Field of Classification Search
CPC .. G01N 27/4065; G01N 27/26; G01N 27/409; G01N 33/007; G01M 15/102;
(Continued)

(56) References Cited

U.S. PATENT DOCUMENTS 4,366,039 A * 12/1982 Uchida .............. G01N 27/4065
204/406
4,609,452 A * 9/1986 Shimomura ....... G01N 27/4065
204/412

(Continued)

FOREIGN PATENT DOCUMENTS

CN     202750273     2/2013
JP     S61-118653    6/1986
(Continued)

OTHER PUBLICATIONS

International Search Report for PCT/JP2014/004014 dated Nov. 11, 2014, five pages.
(Continued)

*Primary Examiner* — David Bolduc
(74) *Attorney, Agent, or Firm* — Nixon & Vanderhye P.C.

(57) ABSTRACT

An $O_2$ sensor has a sensor element, which includes a solid electrolyte layer and a pair of electrodes, while the solid electrolyte layer is interposed between the electrodes. The $O_2$ sensor outputs an electromotive force signal in response to an air-to-fuel ratio of exhaust gas of an engine, which serves as a sensing subject. A constant current circuit, which induces a flow of a predetermined constant electric current between the pair of electrodes of a sensor element, and a current sensing arrangement, which senses a current value of an actual electric current that is conducted through the sensor element, are provided. A microcomputer determines whether an abnormality of the constant current circuit is present based on the current value of the electric current, which is sensed with the current sensing arrangement, in a (Continued)

case where the constant current is induced by the constant current circuit.

7 Claims, 7 Drawing Sheets

(51) Int. Cl.
    *F01N 13/00*           (2010.01)
    *G01M 15/10*          (2006.01)
    *G01N 33/00*          (2006.01)
    *G01N 27/409*         (2006.01)
    *G01N 27/26*          (2006.01)

(52) U.S. Cl.
    CPC .......... *G01M 15/102* (2013.01); *G01N 27/26* (2013.01); *G01N 27/409* (2013.01); *G01N 27/4065* (2013.01); *G01N 33/007* (2013.01); *F01N 2550/02* (2013.01)

(58) Field of Classification Search
    CPC .... F01N 11/007; F01N 11/002; F01N 13/008; F01N 2550/02
    See application file for complete search history.

(56) References Cited

U.S. PATENT DOCUMENTS

| | | | | |
|---|---|---|---|---|
| 4,609,453 | A * | 9/1986 | Shimomura | G01N 27/4065 204/412 |
| 4,724,814 | A * | 2/1988 | Mieno | G01N 27/417 123/688 |
| 4,724,815 | A * | 2/1988 | Mieno | F02D 41/1495 123/690 |
| 5,228,426 | A * | 7/1993 | Pursifull | F02D 41/1494 123/690 |
| 5,340,462 | A * | 8/1994 | Suzuki | F02D 41/1481 123/688 |
| 6,120,677 | A * | 9/2000 | Yamada | F02D 41/1494 204/408 |
| 6,788,128 | B2 * | 9/2004 | Tsuchida | H03K 17/0822 327/309 |
| 7,535,739 | B2 * | 5/2009 | Kidokoro | H03K 17/08104 323/222 |
| 2004/0099530 | A1 * | 5/2004 | Bolz | G01N 27/4065 204/406 |
| 2004/0217001 | A1 * | 11/2004 | Hada | G01N 27/4071 204/424 |
| 2004/0221641 | A1 * | 11/2004 | Moritsugu | G01N 33/007 73/23.31 |
| 2004/0238378 | A1 * | 12/2004 | Kumazawa | G01N 33/0037 205/781 |
| 2005/0029098 | A1 * | 2/2005 | Aoki | G01N 27/4065 204/406 |
| 2005/0288847 | A1 * | 12/2005 | Inoue | G01N 27/4175 701/114 |
| 2006/0157348 | A1 * | 7/2006 | Inoue | F02D 41/1494 204/401 |
| 2006/0219555 | A1 * | 10/2006 | Inagaki | F02D 41/1443 204/426 |
| 2008/0060941 | A1 * | 3/2008 | Ieda | G01N 27/4065 204/431 |
| 2008/0262704 | A1 * | 10/2008 | Kawase | F01N 9/00 701/109 |
| 2009/0128157 | A1 * | 5/2009 | Moriya | G01R 31/3624 324/426 |
| 2012/0043205 | A1 | 2/2012 | Matsuoka et al. | |
| 2012/0176117 | A1 * | 7/2012 | Watanabe | H03K 17/08 323/312 |
| 2012/0188001 | A1 * | 7/2012 | Mizobe | H02P 29/02 327/427 |
| 2012/0217937 | A1 * | 8/2012 | Miyauchi | H03K 17/18 322/28 |
| 2013/0199485 | A1 * | 8/2013 | Shibata | F02P 17/12 123/146.5 R |
| 2014/0373512 | A1 | 12/2014 | Yokoi et al. | |
| 2015/0025778 | A1 * | 1/2015 | Matsuoka | G01N 27/4065 701/104 |
| 2015/0041318 | A1 | 2/2015 | Yamada et al. | |
| 2015/0041319 | A1 | 2/2015 | Yamada et al. | |
| 2015/0041320 | A1 | 2/2015 | Yamada et al. | |
| 2015/0041334 | A1 | 2/2015 | Matsuoka et al. | |

FOREIGN PATENT DOCUMENTS

| | | | |
|---|---|---|---|
| JP | WO 2013114815 A1 * | 8/2013 | ......... G01N 27/4065 |
| WO | WO 2013/114815 | 8/2013 | |
| WO | WO 2014/196131 | 12/2014 | |

OTHER PUBLICATIONS

Written Opinion of the ISA for PCT/JP2014/004014 dated Nov. 11, 2014, eight pages.

* cited by examiner

GAS SENSOR CONTROL DEVICE

CROSS REFERENCE TO RELATED APPLICATION

The present application is the U.S. national phase of International Application No. PCT/JP2014/004014 filed on Jul. 31, 2014 and is based on and incorporates herein by reference Japanese Patent Application No. 2013-167128 filed on Aug. 9, 2013.

The present application is based on and incorporates herein by reference Japanese Patent Application No. 2013-167128 filed on Aug. 9, 2013.

TECHNICAL FIELD

The present disclosure relates to a gas sensor control device.

BACKGROUND ART

For instance, a gas sensor, which outputs an electromotive force, is provided at a vehicle engine. In this type of gas sensor, exhaust gas, which is discharged from the engine, serves as a sensing subject of the gas sensor, and an oxygen concentration of the exhaust gas is sensed with the gas sensor. This type of gas sensor includes an electromotive force cell, which outputs an electromotive force signal that varies depending on whether the exhaust gas is rich or lean. Specifically, when an air-to-fuel ratio is rich, the electromotive force cell outputs the electromotive force signal of about 0.9 V. In contrast, when the air-to-fuel ratio is lean, the electromotive force cell outputs the electromotive force signal of about 0 V.

In this type of gas sensor, when the air-to-fuel ratio of the exhaust gas changes between rich and lean, a change in the sensor output may be disadvantageously delayed relative to an actual change in the air-to-fuel ratio. In order to improve the output characteristic of such a gas sensor, various techniques have been proposed.

For instance, the Patent Literature 1 discloses a gas sensor control device, in which a constant current circuit is connected to at least one of a pair of sensor electrodes. In this gas sensor control device, when it is determined that a demand for changing the output characteristic of the gas sensor is present, a flow direction of the constant electric current is determined based on the demand. Then, the constant current circuit is controlled to induce a flow of the constant electric current in the determined direction. Through the supply of the constant electric current, the output characteristic of the gas sensor is appropriately controlled.

The air-to-fuel ratio control operation, which uses the sensed value of the gas sensor, significantly contributes to the reduction of the exhaust emissions of the engine. In a case where an abnormality is present in the gas sensor, the abnormality has a significant influence with respect to the reduction of the exhaust emissions. Furthermore, even in a case where the gas sensor is normal, when the constant electric current does not normally flow in the electromotive force cell, it may possibly have an influence on the exhaust emissions. With respect to the above point, it is desirable to correctly determine whether an abnormality is present in the constant current circuit.

CITATION LIST

Patent Literature

PATENT LITERATURE 1: JP2012-63345A (corresponding to US201210043205A1)

SUMMARY OF INVENTION

It is a major objective of the present disclosure to provide a gas sensor control device that can appropriately sense an abnormality in a constant current circuit, which induces a flow of a constant current in a gas sensor, and thereby to improve a reliability of a gas sensor output.

Hereinafter, means for solving the above objective and advantages thereof will be described.

The present disclosure provides a gas sensor control device applied to an exhaust gas purifying device of an internal combustion engine, which includes: a catalyst that is installed in an exhaust device of the internal combustion engine and purifies NOx, which is a lean component of an exhaust gas of the internal combustion engine, and a rich component of the exhaust gas; and a gas sensor that is installed at a location, which is in an intermediate portion of the catalyst or on a downstream side of the catalyst, to sense a gas component of the exhaust gas, which serves as a sensing subject, after purification of the exhaust gas with the catalyst, wherein the gas sensor includes an electromotive force cell, which has a solid electrolyte body and a pair of electrodes, to output an electromotive force signal in response to an air-to-fuel ratio of the exhaust gas. The gas sensor control device includes: a current conduction regulating device that induces a flow of a predetermined constant electric current between the pair of electrodes of the electromotive force cell; a current sensing arrangement that senses a current value of an actual electric current, which is conducted through the electromotive force cell; and an abnormality determining unit that determines whether an abnormality is present in the current conduction regulating device based on the current value of the actual electric current, which is sensed with the current sensing arrangement, in a case where the flow of the predetermined constant electric current is induced by the current conduction regulating device.

The above construction is made in view of that even in the case where the gas sensor is normal, when the constant electric current does not normally flow through the electromotive force cell, it may possibly have an influence on the exhaust emissions, and thereby the above construction is made to enable the appropriate determination of whether the abnormality is present in the current conduction regulating device (the constant current circuit). In this way, with respect to the gas sensor, which uses the exhaust gas outflowing on the downstream side of the catalyst, i.e., the exhaust gas after the purification thereof at the catalyst as the sensing subject, the reliability of the sensor output of the gas sensor can be improved. Particularly, in the case where the abnormality occurs in the current conduction regulating device (the constant current circuit), it is desirable that the occurrence of the abnormality can be detected in the early stage in order to minimize the influence on the exhaust emissions. With respect to this point, in the case where the actual current value of the electric current, which is induced by the current conduction regulating device, is monitored, and the abnormality determination is made based on the actual current value of the electric current, the abnormality determination can be always made regardless of the operational state of the internal combustion engine. Thereby, it is possible to implement the practically desirable construction.

DESCRIPTION OF EMBODIMENTS

Figure 1:
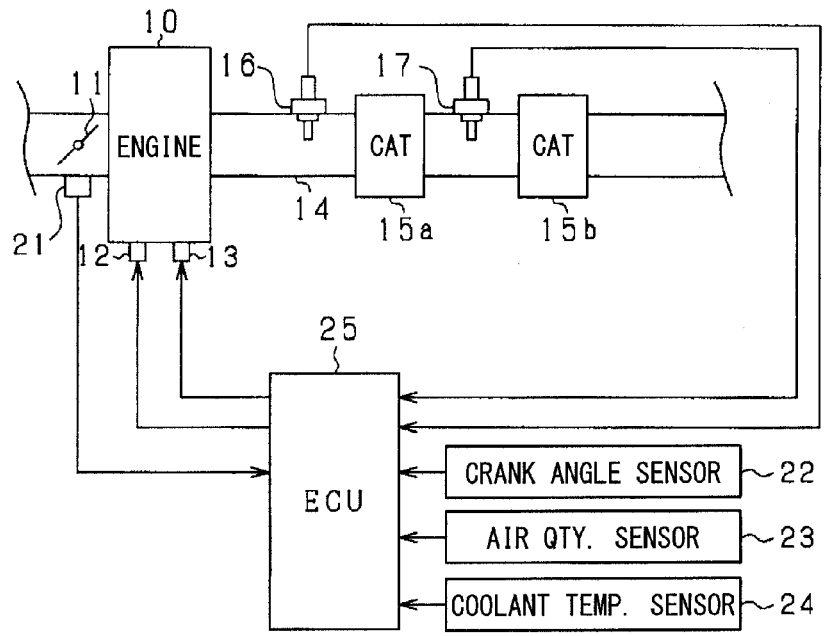
FIG. 1 is a diagram schematically showing an entire structure of an engine control system according to an embodiment of the present disclosure.

An embodiment of the present disclosure will be described with reference to the accompanying drawings. In the present embodiment, a gas sensor, which is provided in an exhaust conduit of an engine (internal combustion engine) of a vehicle, is used, and there will be described an engine control system, which executes various control operations of the engine based on an output of the gas sensor. In the control system, an electronic control unit (hereinafter referred to as an ECU) is used to execute, for example, a control operation of a fuel injection quantity and a control operation of ignition timing. FIG. 1 is a diagram that schematically shows an entire structure of the system.

In FIG. 1, the engine 10 is, for example, a gasoline engine and has an electronically controlled throttle valve 11, fuel injection valves 12, and ignition devices 13. Catalysts 15a, 15b, which serve as an exhaust gas purifying device, are installed in an exhaust conduit 14 (serving as an exhaust device) of the engine 10. Each of the catalysts 15a, 15b is formed as, for example, a three-way catalyst. The catalyst 15a is a first catalyst, which serves as an upstream side catalyst, and the catalyst 15b is a second catalyst, which serves as a downstream side catalyst. As is well known in the art, the three-way catalyst purifies three noxious components of the exhaust gas, i.e., CO (carbon monoxide), HC (hydrocarbon) and NOx (nitrogen oxide, such as NO) and is formed by applying metal, such as platinum, palladium, rhodium, to a ceramic substrate that is configured into, for example, a honeycomb form or a lattice form. In this instance, at the three-way catalyst, CO and HC, which are the rich components, are purified through an oxidation reaction, and NOx, which is the lean component, is purified through a reduction reaction.

An A/F sensor 16 is placed on an upstream side of the first catalyst 15a, and an $O_2$ sensor (oxygen sensor) 17 is placed between the catalysts 15a, 15b (on the downstream side of the first catalyst 15a and on the upstream side of the second catalyst 15b). The A/F sensor 16 outputs an A/F signal, which is generally proportional to the air-to-fuel ratio of the exhaust gas. Furthermore, the $O_2$ sensor 17 outputs an electromotive force signal, which varies depending on whether the air-to-fuel ratio of the exhaust gas is rich or lean.

Furthermore, the system is provided with various sensors, such as a throttle opening degree sensor 21, which senses the opening degree of the throttle valve 11, a crank angle sensor 22, which outputs a crank angle signal of a rectangular waveform at every predetermined crank angle (e.g., a period of 30 degree crank angle) of the engine, an air quantity sensor 23, which senses the quantity of the intake air drawn into the engine 10, and a coolant temperature sensor 24, which senses the temperature of the engine coolant. Although not depicted in the drawings, besides the above sensors, there are also provided, for example, a combustion pressure sensor, which senses a combustion pressure in a cylinder of the engine, an accelerator opening degree sensor, which senses an opening degree of an accelerator (an accelerator manipulation amount), and an oil temperature sensor, which senses a temperature of an engine lubricating oil. These sensors respectively serve as an operational state sensing means.

The ECU 25 includes a microcomputer of a known type, which has, for example, a CPU, a ROM, and a RAM. The ECU 25 executes various control programs, which are stored in the ROM, to perform various control operations of the engine 10 according to the engine operational state. Specifically, the ECU 25 receives signals from the above-described sensors, and the ECU 25 computes each corresponding fuel injection quantity and each corresponding ignition timing to execute, for example, the control operation for driving the fuel injection valves 12 and the control operation for driving the ignition devices 13 based on the signals.

Particularly, with respect to the fuel injection quantity control operation, the ECU 25 performs an air-to-fuel ratio feedback control operation based on a measurement signal of the A/F sensor 16, which is placed on the upstream side of the first catalyst, and a measurement signal of the $O_2$ sensor 17, which is placed on the downstream side of the first catalyst. Specifically, the ECU 25 executes a main feedback control operation in such a manner that an actual air-to-fuel ratio (an actual air-to-fuel ratio at the location on the upstream side of the first catalyst), which is sensed with the A/F sensor 16, coincides with a target air-to-fuel ratio, which is set based on the engine operational state. Also, the ECU 25 executes a sub-feedback control operation in such a manner that an actual air-to-fuel ratio (an actual air-to-fuel ratio at the location on the downstream side of the first catalyst), which is sensed with the $O_2$ sensor 17, coincides with a target air-to-fuel ratio. In the sub-feedback control operation, in view of, for example, a difference between the actual air-to-fuel ratio on the downstream side of the first catalyst and the target air-to-fuel ratio, the target air-to-fuel ratio used in the main feedback control operation is corrected, or a feedback correction amount used in the main feedback control operation is corrected. The ECU 25 executes a stoichiometric feedback control operation, which sets the target air-to-fuel ratio to a stoichiometric air-to-fuel ratio (theoretical air-to-fuel ratio), as the air-to-fuel ratio control operation.

Figure 2:
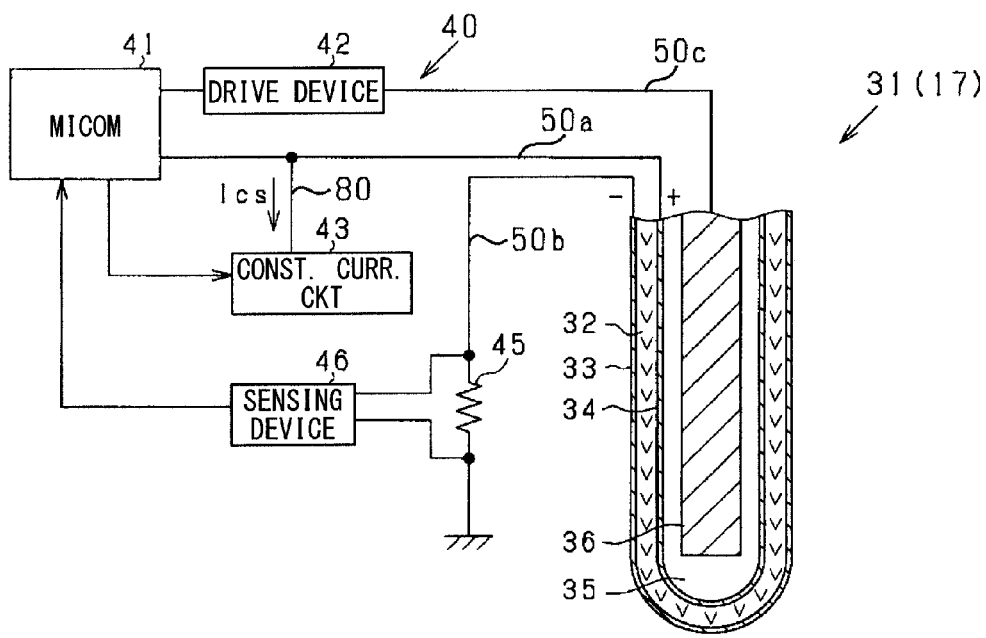
FIG. 2 is a diagram schematically showing a cross section of a sensor element and a sensor control arrangement of the embodiment.

Next, the structure of the $O_2$ sensor 17, which is placed on the downstream side of the first catalyst, will be described. The $O_2$ sensor 17 has a sensor element 31, which is configured into a cup shape. FIG. 2 shows a cross section of the sensor element 31. In reality, the sensor element 31 is configured such that the entire sensor element 31 is received in a housing or an element cover, and the sensor element 31 is placed in the exhaust conduit 14. The sensor element 31 serves as an electromotive force cell.

In the sensor element 31, a solid electrolyte layer 32, which serves as a solid electrolyte body, has a cup shaped cross section. An exhaust side electrode 33 is formed in an outer surface of the solid electrolyte layer 32, and an atmosphere side electrode 34 is formed in an inner surface of the solid electrolyte layer 32. Each of the electrodes 33, 34 is formed as a layer on the corresponding surface of the solid electrolyte layer 32. The solid electrolyte layer 32 is an oxide sintered body, which conducts oxygen ions therethrough and is formed by completely dissolving CaO, MgO, $Y_2O_3$, and/or $Yb_2O_3$ as stabilizer into $ZrO_2$, $HfO_2$, $ThO_2$, and/or $Bi_2O_3$. Furthermore, each electrode 33, 34 is made of a noble metal, such as platinum, which has the high catalytic activity, and a surface of the electrode 33, 34 is covered with a porous coating that is chemically plated. The above-described electrodes 33, 34 serve as a pair of electrodes (sensor electrodes). An inside space, which is surrounded by the solid electrolyte layer 32, is an atmosphere chamber (a reference gas chamber) 35. A heater 36 is received in the atmosphere chamber 35. The heater 36 has a sufficient heat capacity to activate the sensor element 31, and the sensor element 31 is entirely heated by a heat energy, which is generated from the heater 36. An activation temperature of the $O_2$ sensor 17 is, for example, 500 to 650 degrees Celsius. The atmosphere gas is introduced into the atmosphere chamber 35, so that the inside of the atmosphere chamber 35 is maintained at a predetermined oxygen concentration.

In the sensor element 31, the exhaust gas is present at the outside (the electrode 33 side) of the solid electrolyte layer 32, and the atmosphere gas is present at the inside (the electrode 34 side) of the solid electrolyte layer 32. An electromotive force is generated between the electrode 33 and the electrode 34 in response to a difference in an oxygen concentration (a difference in an oxygen partial pressure) between the outside (the electrode 33 side) of the solid electrolyte layer 32 and the inside (the electrode 34 side) of the solid electrolyte layer 32. Specifically, the generated electromotive force varies depending on whether the air-to-fuel ratio is rich or lean. In such a case, the oxygen concentration at the exhaust side electrode 33 is lower than the oxygen concentration at the atmosphere side electrode 34, which serves as a reference side electrode, and the electromotive force is generated at the sensor element 31 while the atmosphere side electrode 34 and the exhaust side electrode 33 serve as a positive side and a negative side, respectively. Thus, the $O_2$ sensor 17 outputs the electromotive force signal, which corresponds to the oxygen concentration (the air-to-fuel ratio) of the exhaust gas.

Figure 3:
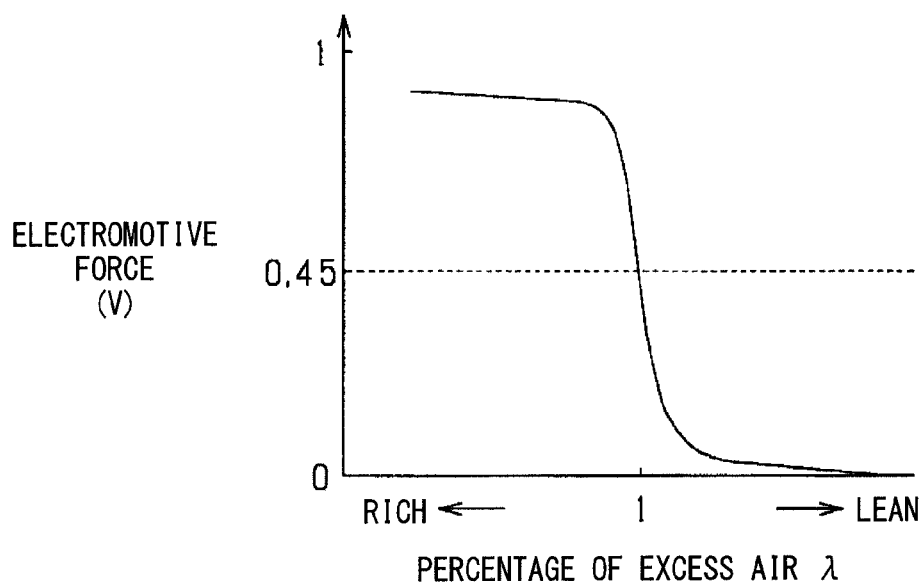
FIG. 3 is an electromotive force characteristic diagram indicating a relationship between an air-to-fuel ratio and an electromotive force of the sensor element.

FIG. 3 is an electromotive force characteristic diagram showing a relationship between the air-to-fuel ratio of the exhaust gas and the electromotive force of the sensor element 31. In FIG. 3, the axis of abscissas indicates a percentage of excess air $\lambda$. When the percentage of excess air $\lambda$ is 1 (i.e., $\lambda=1$), the air-to-fuel ratio is the stoichiometric air-to-fuel ratio (theoretical air-to-fuel ratio). The sensor element 31 has the characteristics of that the electromotive force generated from the sensor element 31 varies depending on whether the air-to-fuel ratio is rich or lean, and the electromotive force generated from the sensor element 31 rapidly changes around the stoichiometric air-to-fuel ratio. Specifically, the electromotive force of the sensor element 31 at the rich time is about 0.9 V, and the electromotive force of the sensor element 31 at the lean time is about 0 V.

In FIG. 2, a sensor control arrangement 40 is connected to the sensor element 31. When the electromotive force is generated at the sensor element 31 in response to the air-to-fuel ratio (the oxygen concentration) of the exhaust gas, the sensor measurement signal (the electromotive force signal), which corresponds to the electromotive force generated at the sensor element 31, is outputted from the sensor element 31 to a microcomputer 41 of the sensor control arrangement 40. The microcomputer 41 computes the air-to-fuel ratio based on the electromotive force signal of the sensor element 31. The sensor control arrangement 40 is formed in the ECU 25 of FIG. 1. At the ECU 25, the microcomputer 41 is formed as a computing means that has an engine control function and a sensor control function. In this case, the microcomputer 41 computes the engine rotational speed and the intake air quantity based on the measurement results of the various sensors discussed above. However, the ECU 25 may be constructed to have an engine control microcomputer, which executes the engine control function, and a sensor control microcomputer, which executes the sensor control function, if desired.

Furthermore, the microcomputer 41 determines an activated state of the sensor element 31 and controls the driving operation of the heater 36 through a drive device 42, which is connected to the heater 36 through an electric path 50c, based on a result of determination of the activated state of the sensor element 31. The technique of the activation determination of the sensor element 31 and the technique of the heater control are already known. Therefore, the activation determination of the sensor element 31 and the heater control will be briefly described. The microcomputer 41 periodically changes the voltage or the electric current applied to the sensor element 31 in a manner that is similar to an alternating current and senses a thus generated change in the electric current or a thus generated change in the electric voltage. A resistance of the sensor element 31 (an impedance of the sensor element 31) is computed based on the change in the electric current or the change in the voltage, and the energization control operation of the heater 36 is executed based on the resistance of the sensor element 31. At that time, there is a correlation between the activated state of the sensor element 31 (the temperature of the sensor element 31) and the resistance of the sensor element 31. When the resistance of the sensor element 31 is controlled to a predetermined target value, the sensor element 31 is held in the desired activated state (the state, under which the activation temperature of the sensor element 31 is held in a range of 500 to 650 degrees Celsius). For example, a sensor element temperature feedback control operation may be executed as the heater control operation.

When the engine 10 is operated, the actual air-to-fuel ratio of the exhaust gas is changed. For example, the air-to-fuel ratio may be repeatedly changed between rich and lean. At the time of changing the actual air-to-fuel ratio between rich and lean, when a deviation exists between the output of the $O_2$ sensor 17 and the presence of NOx, which is the lean component, the emission performance may possibly be influenced. For example, the amount of NOx in the exhaust gas may possibly be increased beyond the intended amount at the time of operating the engine 10 under the high load (the time of accelerating the vehicle).

Figure 4:
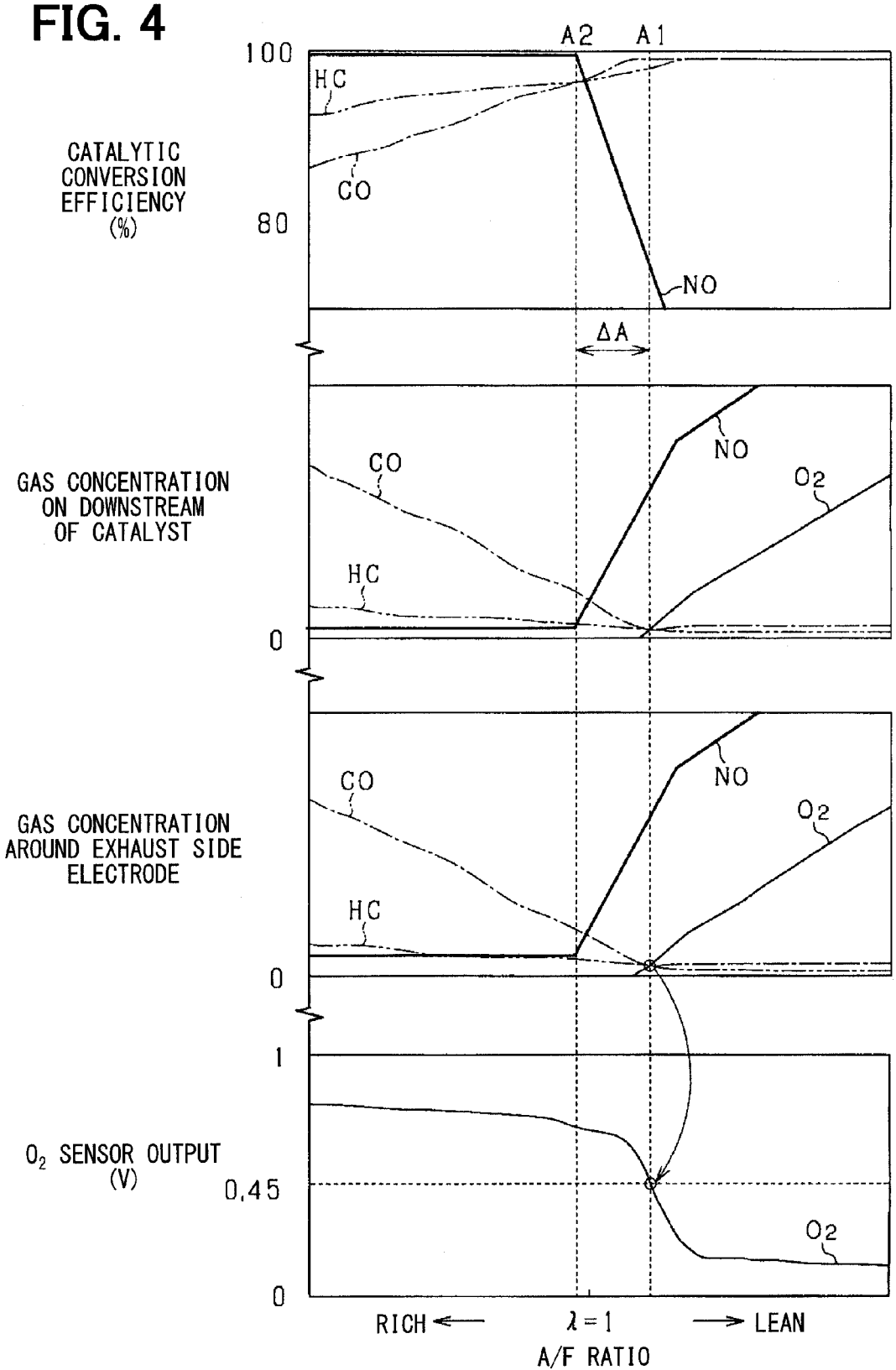
FIG. 4 is a diagram showing catalytic conversion characteristics of a first catalyst and output characteristics of an $O_2$ sensor.

In the present embodiment, a sensing mode of the $O_2$ sensor 17 is changed based on the relationship between the output characteristic of the $O_2$ sensor 17, which outputs the electromotive force, and the catalytic conversion characteristic of the first catalyst 15a, which is placed on the upstream side of the $O_2$ sensor 17. Details of the change of the sensing mode of the $O_2$ sensor 17 will be described later. FIG. 4 is a diagram that shows the catalytic conversion characteristics of the first catalyst 15a, which is the three-way catalyst, and the output characteristics of the $O_2$ sensor 17. Specifically, FIG. 4 shows: a relationship between a catalytic conversion efficiency of each of the three noxious components (i.e., CO, HC, NOx) of the exhaust gas at the first catalyst 15a and the air-to-fuel ratio; a relationship between the gas concentration of each of the three noxious components and the oxygen on the downstream side of the first catalyst 15a and the air-to-fuel ratio; a relationship between the gas concentration of each of the three noxious components and the oxygen around the surface of the exhaust side electrode 33 of the $O_2$ sensor 17 and the air-to-fuel ratio; and a relationship between the electromotive force output of the $O_2$ sensor 17 and the air-to-fuel ratio.

The first catalyst (the three-way catalyst) 15a has a catalytic conversion window, in which the catalytic conversion efficiency of each of the three noxious components becomes high around the point of the stoichiometric air-to-fuel ratio (percentage of excess air $\lambda=1$), as is known in the art. Furthermore, with respect to the concentrations of the three noxious components and the concentration of the oxygen on the downstream side of the first catalyst 15a, it is understood that a reaction equilibrium point A1, at which the concentrations of the rich components (CO, HC) and the concentration of the oxygen become generally equal to one another, is present around the point of the stoichiometric air-to-fuel ratio, and an NOx outflow point A2, at which NOx (NO) begins to outflow from the first catalyst 15a on the downstream side of the first catalyst 15a, is also present. In this case, it is understood that the NOx outflow point A2 (the point of starting the outflow of NOx from the catalyst 15a) is located on the rich side of the reaction equilibrium point A1, and the NOx outflow point A2 and the reaction equilibrium point A1 are spaced from each other by a difference $\Delta A$. That is, the first catalyst 15a has the catalytic conversion characteristic of that the NOx outflow point (serving as a second air-to-fuel ratio point) A2, at which NOx begins to outflow from the first catalyst 15a, is located on the rich side of the reaction equilibrium point (serving as a first air-to-fuel ratio point) A1, which forms the equilibrium point for the rich components and the oxygen. It could be said that the reaction equilibrium point A1 is an inflection point of the equilibrium characteristic of the rich components and the oxygen, and the NOx outflow point A2 is an inflection point of the outflow concentration characteristic of NOx.

The reason for the generation of the deviation between the point A1 and the point A2 may be as follows. In the case where the exhaust gas, which contains CO, HC, NOx, and $O_2$, is guided to the first catalyst 15a during the operation of the engine 10, NOx may possibly outflow from the first catalyst 15a in addition to CO and HC. For example, even in the range of the catalytic conversion window of the three-way catalyst, it will be noted that some amount of CO, HC, and NOx outflows from the first catalyst 15a when the amount of CO, HC, and NOx is precisely measured. In such a case, although $O_2$ outflows from the first catalyst 15a in equilibrium with CO and HC (starting of the outflow of $O_2$ at the concentration of CO and HC$\approx$0), NOx outflows from the first catalyst 15a on the downstream side thereof regardless of the reaction of CO and HC. Therefore, the deviation exists between the point A1 and the point A2.

Furthermore, the concentrations of the above three components and the oxygen around the exhaust side electrode of the $O_2$ sensor 17 are the same as the concentrations of the above three components and the oxygen on the downstream side of the first catalyst 15a. In this case, the amount of the rich components (CO, HC) is larger than the amount of oxygen on the rich side of the point A1, and the amount of oxygen is larger than the amount of the rich components on the lean side of the point A1. Therefore, in terms of the electromotive force of the $O_2$ sensor 17, one of a rich signal (0.9 V) and a lean signal (0 V) is outputted on one side or the other side of the reaction equilibrium point A1 of the first catalyst 15a. In this case, it can be said that the reaction equilibrium point for the rich components and the oxygen at the $O_2$ sensor 17 coincides with the reaction equilibrium point A1 at the first catalyst 15a. Furthermore, NOx is present on the rich side of the point A1.

At the exhaust side electrode of the $O_2$ sensor 17, the oxidation reaction and the reduction reaction of CO, HC and NOx of the exhaust gas take place according to the following chemical reaction formulae (1) to (3).

$$CO + 0.5O_2 \rightarrow CO_2 \qquad (1)$$

$$CH_4 + 2O_2 \rightarrow CO_2 + 2H_2O \qquad (2)$$

$$CO + NO \rightarrow CO_2 + 0.5N_2 \qquad (3)$$

Furthermore, there is established a relationship of k1, k2>>K3 where k1, k2 and k3 denote an equilibrium constant of the chemical reaction formula (1), an equilibrium constant of the chemical reaction formula (2), and an equilibrium constant of the chemical reaction formula (3), respectively.

In this case, at the $O_2$ sensor 17, the equilibrium point (the point at which the electromotive force output=0.45 V) is determined through the gas reactions of, for example, CO, HC NOx, and $O_2$. However, due to the differences in the equilibrium constant, the reactions of CO and HC with $O_2$ become main reactions at the exhaust side electrode 33.

Furthermore, the above difference $\Delta A$ is present in the catalytic conversion characteristic of the first catalyst 15a, and the above difference $\Delta A$ has the influence on the output characteristic of the $O_2$ sensor 17. Therefore, in some cases, even when NOx outflows from the first catalyst 15a, the output of the $O_2$ sensor 17 may not correspond to the outflow of NOx from the first catalyst 15a. Thus, the outflow of NOx from the first catalyst 15a cannot be correctly monitored, and thereby the amount of NOx emissions may possibly be increased.

Figure 5:
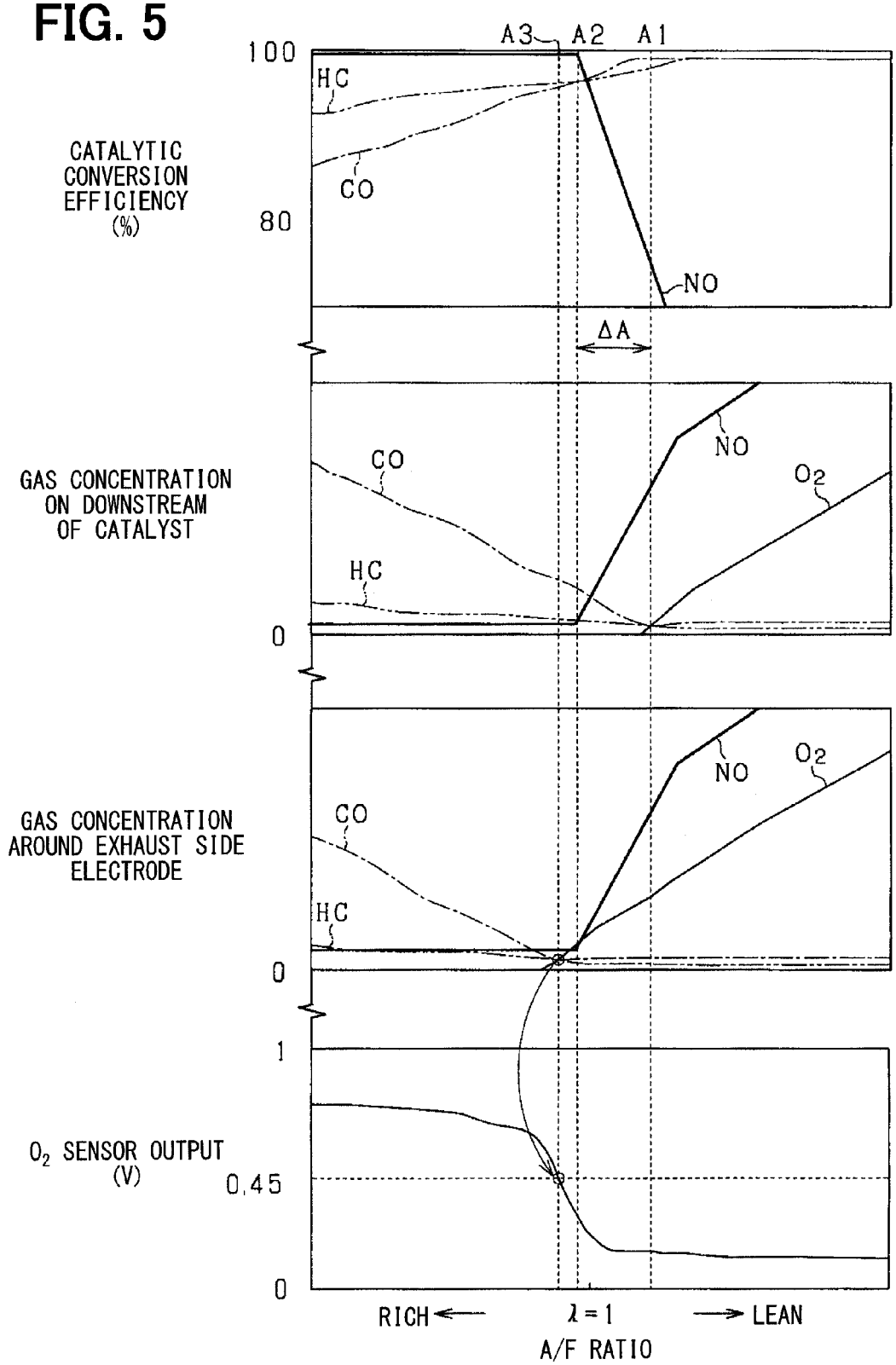
FIG. 5 is a diagram showing catalytic conversion characteristics of the first catalyst and output characteristics of an $O_2$ sensor.

In view of the above disadvantage, according to the present embodiment, the electric current, which has a predetermined current value, is conducted between the electrodes 33, 34 of the sensor element 31 of the $O_2$ sensor 17, so that at the location around the exhaust side electrode of the $O_2$ sensor 17, the concentrations of the rich components are reduced, and the concentration of the oxygen is increased. Specifically, as shown in FIG. 5, the equilibrium point of the gas reaction around the exhaust side electrode of the $O_2$ sensor 17 is changed from the point A1 to a point A3. In FIG. 5, in comparison to FIG. 4, all of the concentration characteristics of CO, HC and $O_2$ around the exhaust side electrode of the $O_2$ sensor 17 are shifted to the rich side. In this way, in the case where the output characteristic of the $O_2$ sensor 17 is changed, and NOx outflows from the first catalyst 15a, the output of the $O_2$ sensor 17 can correspond to the outflow of NOx.

Figure 6:
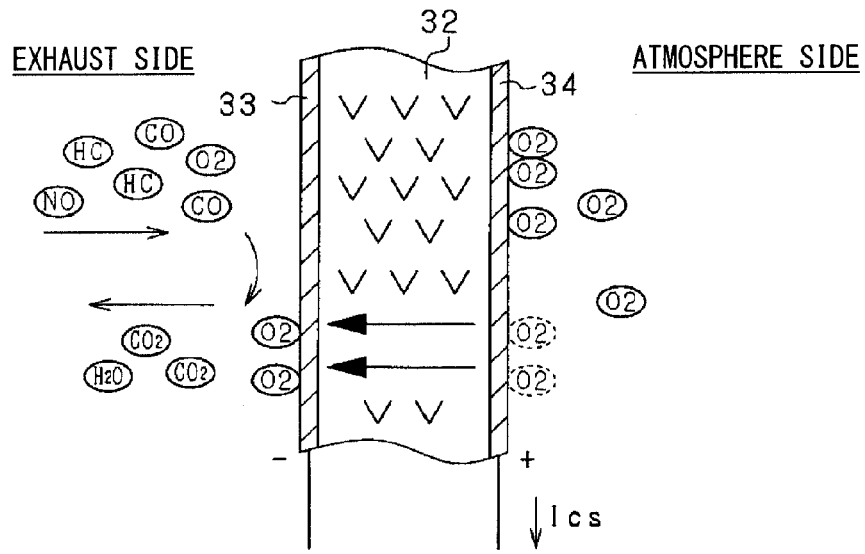
FIG. 6 is a schematic diagram for describing reactions of gas components at the sensor element.

The principle of inducing the change in the sensor output characteristic through conduction of the electric current between the electrodes 33, 34 is as follows. As shown in FIG. 6, CO, HC, NOx and $O_2$ are present around the exhaust side electrode 33 of the $O_2$ sensor 17. Under such a circumstance, the electric current is conducted through the sensor element 31 such that the oxygen ions are moved from the atmosphere side electrode 34 to the exhaust side electrode 33 through the solid electrolyte layer 32. Specifically, the oxygen pumping is executed at the sensor element 31. In this case, at the exhaust side electrode 33, the oxygen, which is moved to the exhaust side electrode 33 side through the solid electrolyte layer 32, reacts with CO and HC to form $CO_2$ and $H_2O$, respectively. In this way, CO and HC are removed around the exhaust side electrode 33, and the equilibrium point of the gas reaction around the exhaust side electrode 33 of the $O_2$ sensor 17 is shifted to the rich side.

Next, the structure of the sensor control arrangement 40, which executes the control operation of the $O_2$ sensor 17, will be described. The structure of the sensor control arrangement 40 is one shown in FIG. 2. Specifically, the sensor control arrangement 40 includes the microcomputer 41, which serves as a control device (control means). The microcomputer 41 obtains the electromotive force signal, which is outputted from the sensor element 31, through, for example, an A/D converter, and the microcomputer 41 computes the air-to-fuel ratio (particularly, the air-to-fuel ratio on the downstream side of the first catalyst) of the exhaust gas based on the obtained electromotive force signal. Furthermore, a constant current circuit 43, which serves as a current conduction regulating device (current conduction regulating means), is connected in an electric path 50a, which electrically connects between the atmosphere side electrode 34 of the sensor element 31 and the microcomputer 41, through an electric path 80. The constant current circuit 43 is configured such that when the sensor element 31 generates the electromotive force, the constant current circuit 43 induces a flow of a predetermined constant electric current through the sensor element 31.

The constant current circuit 43 is configured to enable the flow of the constant electric current Ics from the exhaust side electrode 33 to the atmosphere side electrode 34 through the solid electrolyte layer 32 in the sensor element 31. Furthermore, the constant current circuit 43 has a PWM drive device, and thereby the constant current circuit 43 can adjust a current value of the electric current through a PWM control operation (a duty control operation). The microcomputer 41 sets the current value of the constant electric current of the constant current circuit 43 (the current value of the electric current conducted through the constant current circuit 43) based on a demand for conducting the electric current and controls the constant current circuit 43 to induce the flow of the constant electric current Ics, which has the set current value. Here, it should be noted that the term "current value" refers to a value of the current that is expressed in units of, for example, amperes (A).

In the present embodiment, the control operation of the constant electric current is executed based on a difference between the reaction equilibrium point A1 of the oxygen outflow at the first catalyst 15a and the NOx outflow point A2 of the NOx outflow at the first catalyst 15a. Particularly, the constant electric current is controlled such that the equilibrium point of the gas reaction around the exhaust side electrode of the $O_2$ sensor 17 is placed at the NOx outflow point A2 or a point adjacent to the NOx outflow point A2. In this way, the output characteristic of the $O_2$ sensor 17 is changed based on the catalytic conversion characteristic of the first catalyst 15a. Thereby, when NOx outflows from the first catalyst 15a, the lean signal is outputted at the $O_2$ sensor 17 from the beginning of the outflow of NOx from the first catalyst 15a.

Here, in view of ensuring the robustness of the $O_2$ sensor 17 for the purpose of limiting the NOx emissions, it is desirable that the equilibrium point of the gas reaction around the exhaust side electrode of the $O_2$ sensor 17 is placed on the rich side of the NOx outflow point A2 (see FIG. 5). Specifically, the equilibrium point of the gas reaction around the exhaust side electrode of the $O_2$ sensor 17 may be shifted from the NOx outflow point A2 on the rich side of the NOx outflow point A2 by the amount of, for example, about 0.1 to 0.5% (more desirably 0.1 to 0.3%) in terms of the percentage of excess air $\lambda$ to have a slightly rich state.

When the operational state of the engine 10 is changed, the amount of the rich components in the exhaust gas is changed. Specifically, when the rotational speed of the engine is increased, or when the load of the engine is increased, the amount of the rich components in the exhaust gas is increased. In other words, when the rotational speed or the load of the engine is increased, the flow rate of the rich gas is increased, and the gas concentration of the rich gas is increased. In such a case, when the current value of the electric current to be supplied to the sensor element 31 is kept constant regardless of the engine operational state, the equilibrium point of the gas reaction around the exhaust side electrode of the $O_2$ sensor 17 may possibly be unintentionally deviated from a desirable position, which is set with reference to the NOx outflow point A2. That is, the amount of supplied oxygen, which is supplied around the exhaust side electrode of the sensor element 31 by the supply of the electric current through the sensor element 31, may possibly fall short relative to the amount of the rich components around the exhaust side electrode of the sensor element 31. When this shortage of the supplied oxygen occurs, the rich components remain around the exhaust side electrode 33. Thereby, the output characteristic of the $O_2$ sensor 17 cannot be changed in the desirable manner.

Therefore, in the present embodiment, the current value of the electric current conducted through the sensor element 31 (the current value of the electric current of the constant current circuit 43) is variably controlled based on the operational state of the engine 10. In this case, even when the amount of the required oxygen, which is required to have the equilibrium reaction of the rich gas on the surface of the exhaust side electrode at the $O_2$ sensor 17, is changed in response to the engine operational state, the output characteristic of the $O_2$ sensor 17 can be changed in the desirable manner in response to the change in the amount of the required oxygen. An engine rotational speed, an engine load and/or a load rate of the engine may be used as a parameter (s) of the engine operational state.

Furthermore, in the case where the output characteristic of the $O_2$ sensor 17 is changed by the current value of the electric current of the constant current circuit 43, as discussed above, when an abnormality occurs in the constant current circuit 43, the exhaust emission performance is influenced. Therefore, in the present embodiment, an abnormality determining function, which executes abnormality determination of a determination subject, i.e., the constant current circuit 43, is added to the microcomputer 41.

As shown in FIG. 2, as a structure that is used to sense the abnormality, a shunt resistor 45 for sensing the electric current is connected to the exhaust side electrode 33, and the electric current, which flows through the shunt resistor 45, is sensed with a current sensing device 46. Specifically, the shunt resistor 45 is installed in the electric path 50b, which connects between the exhaust side electrode 33 and the ground. The current sensing device 46 is connected to the exhaust side electrode 33 of the shunt resistor 45 and the ground, and the current, which flows through the shunt resistor 45, is sensed with the current sensing device 46. The current sensing device 46 may include a differential amplifier circuit, which has, for example, an operational amplifier. In this case, the actual current value of the electric current, which is conducted by the constant current circuit 43, is sensed with the shunt resistor 45 and the current sensing device 46, and the microcomputer 41 executes the abnormality determination for determining whether the abnormality is present in the constant current circuit 43 based on the actual current value of the electric current. The shunt resistor 45 and the current sensing device 46 cooperate with each other and serve as a current sensing arrangement of the present disclosure.

Figure 7:
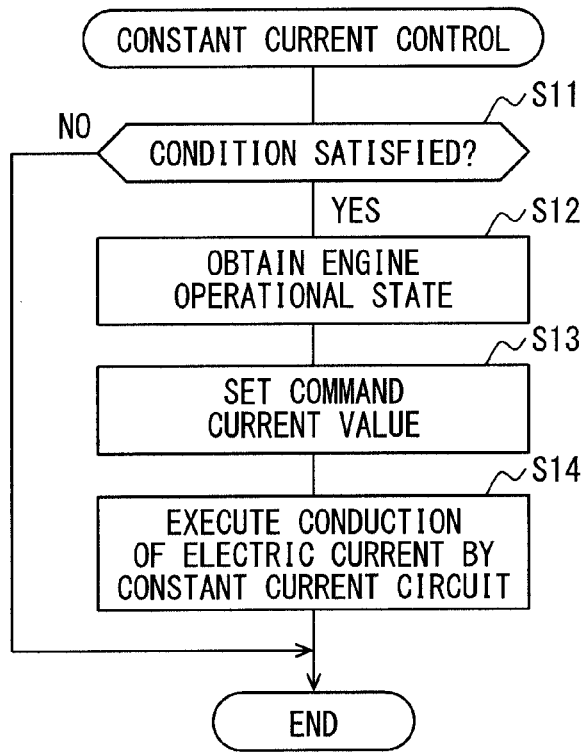
FIG. 7 is a flowchart showing a procedure of a constant electric current control operation of the embodiment.

Next, a constant current control operation and an abnormality determination process, which are executed by the microcomputer 41, will be described with reference to flowcharts. FIG. 7 is the flowchart showing the constant current control operation. This operation is repeated by the microcomputer 41 at predetermined time intervals.

In FIG. 7, at step S11, it is determined whether an execution condition for executing the constant current control operation is satisfied. For instance, the execution condition may include the followings: the $O_2$ sensor 17 and the constant current circuit 43 are both normal; and the sub-feedback control operation is currently executed. When the answer to the inquiry at step S11 is YES, the operation proceeds to step S12.

Figure 8:
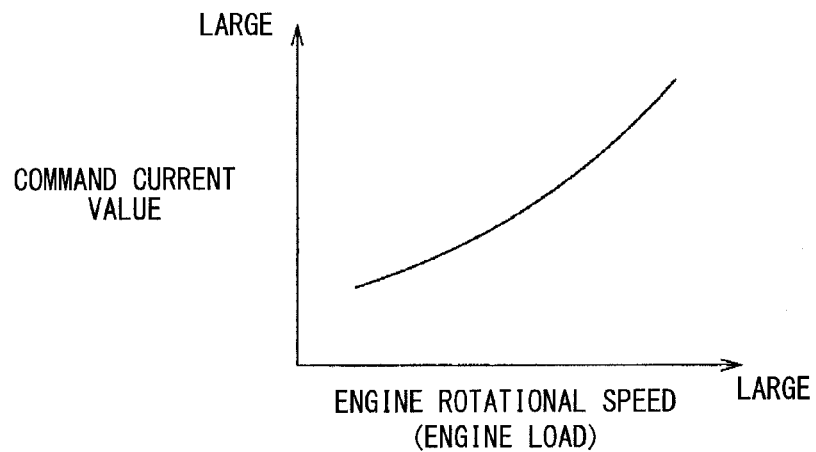
FIG. 8 is a diagram used for setting a command current value of a constant current circuit in the embodiment.

At step S12, the engine operational state, such as the engine rotational speed and/or the engine load (e.g., the amount of the intake air), is obtained. Thereafter, at next step S13, a command current value of the electric current is set based on the engine operational state, which is obtained at step S12. At this time, the command current value of the electric current is set based on, for example, a relationship shown in FIG. 8. In FIG. 8, when the engine rotational speed or the engine load is increased, the command current value of the electric current is increased.

Thereafter, at step S14, the control (control for conduction of electric current) of the constant current circuit 43 is executed such that the constant current circuit 43 induces the flow of the constant electric current, which has the current value set at step S13, through the sensor element 31.

Figure 9:
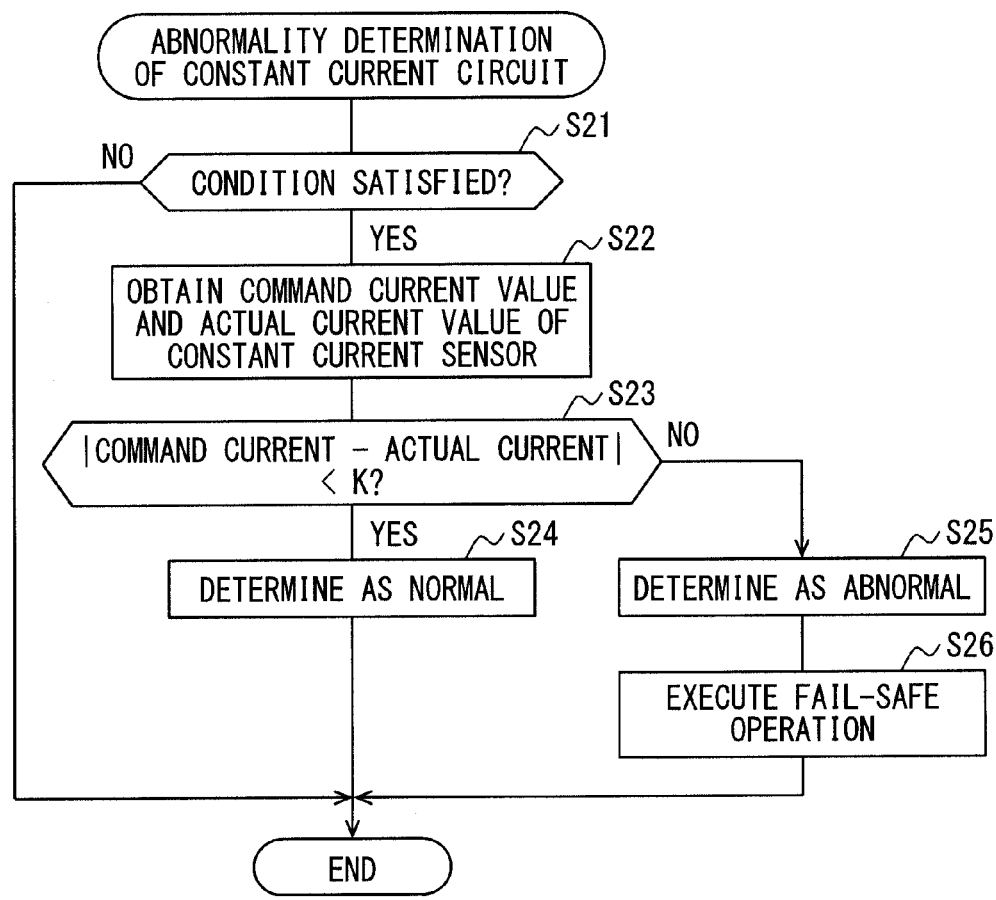
FIG. 9 is a flowchart showing an abnormality determination process for the constant current circuit.

FIG. 9 shows the flowchart indicating the abnormality determination process of the constant current circuit 43. This process is repeated at predetermined time intervals by the microcomputer 41.

In FIG. 9, at step S21, it is determined whether an execution condition for executing the abnormality determination process is satisfied. For example, this execution condition may include a condition of that the sensor element 31 is in the activated state, i.e., the temperature of the sensor element 31 is equal to or higher than the predetermined activation temperature. When the answer to the inquiry at step S21 is YES, the operation proceeds to step S22.

At step S22, the command current value of the electric current for the constant current circuit 43 at this time is obtained, and an actual current value of the electric current, which is sensed with the shunt resistor 45 and the current sensing device 46 at this time, is obtained. At this time, in a case where the command current value has been changed immediately before the time of executing step S22, the actual current value of the electric current should be sensed with the shunt resistor 45 and the current sensing device 46 and is obtained by the microcomputer 41 from the current sensing device 46 after stabilization of the actual current value of the electric current. Specifically, the actual current value is sensed and is obtained by the microcomputer 41 after elapsing of a predetermined time period from the time of changing the command current value.

Then, at step S23, the command current value and the actual current value are compared with each other, and it is determined whether a difference (absolute value of the difference) between the command current value and the actual current value is smaller than a predetermined determination value K. When it is determined that the difference (absolute value of the difference) between the command current value and the actual current value is smaller than the determination value K at step S23, the operation proceeds to step S24 where it is determined that the constant current circuit 43 is normal. In contrast, when it is determined that the difference (absolute value of the difference) between the command current value and the actual current value is equal to or larger than the determination value K at step S23, the operation proceeds to step S25 where it is determined that the constant current circuit 43 is abnormal. Desirably, the determination value K is set in view of a circuit tolerance (e.g., a tolerance of a sensor IC). When it is determined that the constant current circuit 43 is abnormal at step S25, the operation proceeds to step S26. At step S26, there is executed a fail-safe operation, such as stopping of the conduction (supply) of the constant electric current through the constant current circuit 43, stopping of the sub-feedback control operation of the air-to-fuel ratio, turning on of an abnormality warning lamp provided in, for example, an instrument panel, and/or storing of diagnosis data in a storage device.

The microcomputer 41 includes a setting unit, which has a function of setting the command current value by executing steps S11-S13 of the flowchart of FIG. 7, and an abnormality determining unit, which has a function of determining whether the abnormality is present in the constant current circuit 43 by executing steps S21-S25 of the flowchart of FIG. 9. It should be noted that these functions are not necessarily executed by the single microcomputer and may be executed by a plurality of microcomputers.

The present embodiment discussed above provides the following advantages.

Even in the case where the $O_2$ sensor 17 is normal, when the constant electric current does not normally flow through the sensor element 31, it may possibly have an influence on the exhaust emissions. The present embodiment is implemented in view of this point, and there is provided the construction that enables the appropriate determination of whether the abnormality is present in the constant current circuit 43. In this way, the reliability of the output of the $O_2$ sensor can be improved. Particularly, in the case where the abnormality is present in the constant current circuit 43, it is desirable that the presence of the abnormality is detected at an early stage. With respect to this point, the construction, which monitors the actual current value of the electric current induced by the constant current circuit 43 and executes the abnormality determination based on the actual current value of the electric current, can always execute the abnormality determination regardless of, for example, the operational state of the engine 10. Therefore, it is possible to implement the construction that is practically desirable.

The current value (the command current value) of the electric current induced by the constant current circuit 43 is controlled based on the engine operational state. In this way, even when the amount of the rich components in the exhaust gas is changed due to the change in the engine operational state, the output characteristic of the $O_2$ sensor 17 can be appropriately changed, and thereby the equilibrium point of the gas reaction around the exhaust side electrode of the $O_2$ sensor 17 can be maintained at the desired position relative to the NOx outflow point A2.

In the case where the command current value of the electric current is set based on the engine operational state, the abnormality determination, which determines whether the abnormality is present in the constant current circuit 43, is executed based on the result of the comparison between the command current value of the electric current and the actual current value of the electric current. In this way, even when the command current value of the electric current is changed in response to the engine operational state, the appropriate abnormality determination can be executed.

In the state where the sensor element 31 is in the low temperature state (the deactivated state), the resistance of the sensor element 31 is high. In such a state, even though the constant electric current should be normally conducted through the sensor element 31, the actual electric current does not substantially flow through the sensor element 31. With respect to this point, the abnormality determination is executed upon satisfaction of the condition of that the temperature of the sensor element 31 is equal to or higher than the predetermined temperature (the predetermined activation temperature). Therefore, the abnormality determination, which is highly reliable, can be executed.

Through use of the constant current circuit 43, which is constructed in the above-described manner, the output characteristic of the $O_2$ sensor 17 can be adjusted to correspond with the air-to-fuel ratio at the point where the outflow of NOx begins at the first catalyst 15a. That is, in the case where the NOx outflows from the first catalyst 15a, the electromotive force output of the $O_2$ sensor 17, which corresponds to this outflow, is generated. Therefore, the output characteristic of the $O_2$ sensor 17 can be appropriately changed, and thereby the NOx emissions can be limited. Furthermore, when the abnormality determination of the constant current circuit 43 is executed in the above-described manner, the reliability of the sensor output characteristic can be improved at the time of adjusting the sensor output characteristic.

The constant electric current Ics, which is conducted by the constant current circuit 43, shifts the equilibrium point of the gas reaction around the exhaust side electrode of the $O_2$ sensor 17 to the NOx outflow point A2 (the second air-to-fuel ratio point) or the point adjacent to the NOx outflow point A2. Thereby, there is implemented the construction that is more appropriate in terms of limiting the NOx emissions through use of the output of the $O_2$ sensor 17.

Particularly, when the constant electric current Ics is supplied through the constant current circuit 43 in such a manner that the equilibrium point of the gas reaction around the exhaust side electrode of the $O_2$ sensor 17 becomes slightly rich relative to the NOx outflow point A2 (the second air-to-fuel ratio point), the required robustness can be achieved to limit the NOx emissions.

Figure 10:
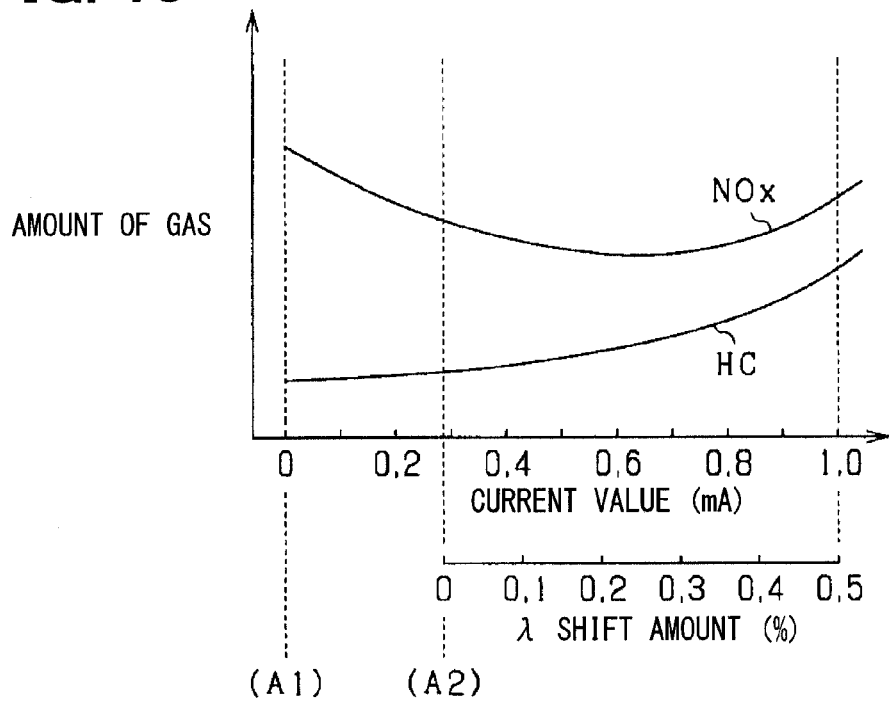
FIG. 10 is a diagram showing a test result with respect to the amount of NOx emissions and the amount of HC emissions on a downstream side of the first catalyst.

FIG. 10 indicates a test result with respect to the amount of emissions of NOx and the amount of emissions of HC on the downstream side of the first catalyst 15a. In FIG. 10, there is indicated the result of the air-to-fuel ratio control operation executed in the state where the output characteristic of the $O_2$ sensor 17 is changed. In FIG. 10, "A1" indicates the reaction equilibrium point A1 at the first catalyst 15a, and "A2" indicates the NOx outflow point A2, and "λ shift amount" indicates a rich change amount in terms of λ (percentage of excess air). In this case, it should be understood that the amount of NOx emissions is reduced in a range where the λ shift amount is 0 to 0.5%. Furthermore, an appropriate value of the λ shift amount is 0.1 to 0.5%. Desirably, the current value of the electric current to be conducted through the sensor element 31 is a value in a rage of 0.1 mA to 1.0 mA.

(Other Embodiments)

The present disclosure is not necessarily limited to the above embodiment, and, for example, the above embodiment may be modified as follows.

Figure 11:
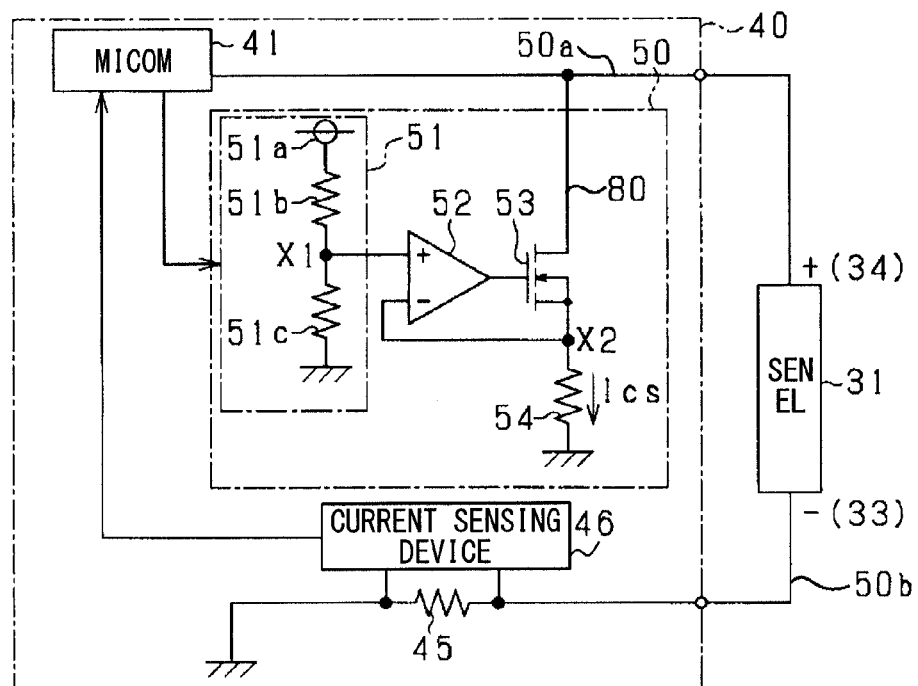
FIG. 11 is a diagram showing a structure of a sensor control arrangement in a modification of the embodiment.

The current conduction regulating device may be constructed to have a structure shown in FIG. 11. In FIG. 11, there is provided a constant current circuit 50 as the current conduction regulating device. When the sensor electromotive force is applied to the constant current circuit 50, the constant current circuit 50 conducts the constant electric current, which corresponds to this electromotive force. The constant current circuit 50 includes a voltage generating arrangement 51, which generates a predetermined constant voltage, an operational amplifier 52, an n-channel MOSFET 53, which is driven by an output of the operational amplifier 52, and a resistor 54, which is connected to a source of the MOSFET 53. The MOSFET 53 and the resistor 54 are connected in series in an electric path 80, which connects between the electric path 50a and the ground. The voltage generating arrangement 51 includes a constant voltage source 51a (e.g., 5 V) and two resistors 51b, 51c. The constant voltage source 51a and the resistors 51b, 51c are connected in series, and an intermediate point between the resistors 51b, 51c forms a voltage output point X1. A + input terminal of the operational amplifier 52 is connected to the voltage output point X1, and an output terminal of the operational amplifier 52 is connected to a gate of the MOSFET 53. Furthermore, a − input terminal of the operational amplifier 52 is connected to an intermediate point X2 between the MOSFET 53 and the resistor 54. The gate, the drain and the source of the MOSFET 53 are connected to the output terminal of the operational amplifier 52, the atmosphere side electrode 34 of the sensor element 31 and the resistor 54, respectively.

The constant current circuit 50, which is constructed in the above-described manner, is operated such that the voltage of the + input terminal of the operational amplifier 52 and the voltage of the − terminal of the operational amplifier 52 become equal to each other. Therefore, the voltage of the intermediate point X2 and the voltage of the voltage output point X1 are equal to each other. The constant electric current Ics, which has a current value determined based on the voltage of the intermediate point X2 and the resistance value of the resistor 54, flows through a series circuit that includes the sensor element 31, the MOSFET 53 and the resistor 54. At this time, the MOSFET 53 is operated in response to an output voltage of the operational amplifier, which is generated due to a difference between the input voltage of the + terminal and the input voltage of the − terminal of the operational amplifier, so that the MOSFET 53 functions as a current control element that conducts the constant electric current Ics.

Desirably, the voltage of the voltage output point X1, the voltage of the intermediate point X2 and the resistance value of the resistor 54 are determined based on the current value of the electric current that needs to be conducted through the sensor element 31 at the time of generating the electromotive force in the sensor element 31. Specifically, in a case where the electric current, which has the current value of 0.1 mA, needs to be conducted through the sensor element 31 at the time of generating the electromotive force (0 to 0.9 V) in the sensor element 31, the voltage of the voltage output point X1 and the voltage of the intermediate point X2 are set to be 10 mV, and the resistance value of the resistor 54 is set to be 100Ω. Furthermore, in a case where the electric current, which has the current value of 0.2 mA, needs to be conducted through the sensor element 31, the voltage of the voltage output point X1 and the voltage of the intermediate point X2 are set to be 20 mV, and the resistance value of the resistor 54 is set to be 100Ω. In addition, in a case where the electric current, which has the current value in a range of 0.1 mA to 1.0 mA, needs to be conducted through the sensor element 31, when the resistance value of the resistor 54 is set to be 100Ω, the voltage of the voltage output point X1 and the voltage of the intermediate point X2 may be set to be in a range of 10 mV to 100 mV. However, in such a case, the reference voltage, which is the voltage of the intermediate point X2 between the MOSFET 53 and the resistor 54 in the constant current circuit 50, is smaller than the electromotive force (0.45 V) of the sensor element 31 generated at the stoichiometric air-to-fuel ratio.

Desirably, the range of the resistance value of the resistor 54 is about 50Ω to 500Ω.

In the sensor control arrangement 40, which has the constant current circuit 50 of the above structure, when the electromotive force is generated in the sensor element 31, the predetermined constant electric current Ics is conducted through the MOSFET 53 and the resistor 54 while using the electromotive force of the sensor element 31 as an electric power source (in other words, the sensor element 31 being used as a battery). Thereby, the output characteristic of the $O_2$ sensor 17 can be changed.

Furthermore, the microcomputer 41 changes, for example, the voltage value (the voltage value at the point X1) of the constant voltage of the voltage generating arrangement 51 based on the engine operational state. In this way, the current value of the electric current conducted through the sensor element 31 (the current value of the electric current conducted through the constant current circuit 50) is variably controlled. In this case, similar to the above embodiment, even when the amount of required oxygen, which is required to have the equilibrium reaction of the rich gas on the surface of the exhaust side electrode 33 at the $O_2$ sensor 17, is changed in response to the engine operational state, the output characteristic of the $O_2$ sensor 17 can be changed in a desirable manner in response to the change in the required oxygen.

In the structure of FIG. 11, the actual current value of the electric current, which is conducted through the sensor element 31, may be sensed, and the abnormality determination, which determines whether the abnormality is present in the constant current circuit 50, may be executed based on the actual current value of the electric current and the command current value of the electric current (the current value of the constant electric current that corresponds to the voltage value at the point X1). The abnormality determination process may be executed by using the above-described construction (FIG. 9), and thereby the description of the abnormality determination process is omitted.

A voltage circuit, which applies a positive voltage to the exhaust side electrode 33, may be provided between the exhaust side electrode 33 of the sensor element 31 and the ground. This voltage circuit may be an offset voltage circuit that raises an electric potential of the exhaust side electrode 33 by a predetermined electric potential relative to an electric potential of the output side of the constant current circuit 43, from which the electric current flows out of the constant current circuit 43. In such a case, the electromotive force outputted from the sensor element 31 has a voltage that is obtained by adding the predetermined offset voltage to the voltage of the original sensor electromotive force (0 to 0.9 V) of the sensor element 31. This construction is particularly advantageous in a case where the sensor element 31 is used as the battery as in the case of FIG. 11. For instance, in the sensor control arrangement 40 of FIG. 11, in the case where the electromotive force of the sensor element 31 changes in the range of 0 to 0.9 V, when the electromotive force becomes small, the current value of the electric current, which is induced by the constant current circuit 50 and is conducted through the sensor element 31, may possibly become smaller than the proper current value. In view of this point, by installing the voltage circuit between the exhaust side electrode 33 and the ground, even in the range where the electromotive force is relatively small, it is possible to limit the excessive reduction of the current value of the electric current, which is induced by the constant current circuit 50 and is conducted through the sensor element 31. Thereby, the output characteristic of the $O_2$ sensor 17 can be appropriately changed.

In the above embodiment (see FIG. 2), the constant current circuit 43 is connected to the atmosphere side electrode 34 among the pair of electrodes 33, 34 of the sensor element 31. This construction may be modified. The constant current circuit 43 may be connected to the exhaust side electrode 33. Alternatively, the constant current circuit 43 may be provided to both of the electrodes 33, 34. In the above embodiment, the $O_2$ sensor 17 is placed on the downstream side of the first catalyst 15a. Alternatively, the $O_2$ sensor 17 may be installed to an intermediate portion of the first catalyst 15a. In such a case, the $O_2$ sensor 17 may be installed to the substrate of the first catalyst 15a. In any of the above cases, it is only required that the $O_2$ sensor 17 is constructed to use the exhaust gas after the purification thereof at the first catalyst 15a as the sensing subject to sense the gas component(s).

Besides the $O_2$ sensor 17 having the above-described structure, the gas sensor may be a gas sensor that has a two-cell structure, which includes an electromotive force cell and a pump cell. In such a case, the output characteristic can be appropriately changed at the electromotive force cell of the two-cell type gas sensor.

The invention claimed is:

1. A gas sensor control device applied to an exhaust gas purifying device of an internal combustion engine, which includes:
    a catalyst that is installed in an exhaust device of the internal combustion engine and purifies NOx, which is a lean component of an exhaust gas of the internal combustion engine, and a rich component of the exhaust gas; and
    a gas sensor that is installed at a location, which is in an intermediate portion of the catalyst or on a downstream side of the catalyst, to sense a gas component of the exhaust gas, which serves as a sensing subject, after purification of the exhaust gas with the catalyst, wherein the gas sensor includes an electromotive force cell, which has a solid electrolyte body and a pair of electrodes, to output an electromotive force signal in response to an air-to-fuel ratio of the exhaust gas, the gas sensor control device comprising:
a current conduction regulating device that induces a flow of a predetermined constant electric current between the pair of electrodes of the electromotive force cell;
a current sensing arrangement that senses a current value of an actual electric current, which is conducted through the electromotive force cell; and
an abnormality determining unit that determines whether an abnormality is present in the current conduction regulating device based on the current value of the actual electric current, which is sensed with the current sensing arrangement, in a case where the flow of the predetermined constant electric current is induced by the current conduction regulating device.

2. The gas sensor control device according to claim 1, further comprising a setting unit that sets a command current value, which is a command value of the electric current to be induced by the current conduction regulating device, wherein the abnormality determining unit determines whether the abnormality is present in the current conduction regulating device based on comparison between the command current value, which is set by the setting unit, and the current value, which is sensed with the current sensing arrangement.

3. The gas sensor control device according to claim 2, wherein the setting unit sets the command current value based on an operational state of the internal combustion engine.

4. The gas sensor control device according to claim 1, wherein the abnormality determining unit determines whether the abnormality is present in the current conduction regulating device based on the current value, which is sensed with the current sensing arrangement, in a case where a temperature of the electromotive force cell is equal to or higher than a predetermined temperature.

5. The gas sensor control device according to claim 1, wherein:
as a catalytic conversion characteristic of the catalyst, which indicates a relationship between an air-to-fuel ratio and a catalytic conversion efficiency of the catalyst, the catalyst has a second air-to-fuel ratio point, which is a point of starting an outflow of the NOx from the catalyst and is located on a rich side of a first air-to-fuel ratio point that forms an equilibrium point for the rich component and oxygen; and
the current conduction regulating device induces the flow of the predetermined constant electric current, which has a current value that corresponds to a difference between the first air-to-fuel ratio point and the second air-to-fuel ratio point at the catalyst.

6. The gas sensor control device according to claim 5, wherein:
one of the pair of electrodes of the electromotive force cell is a reference side electrode, which becomes a positive side at a time of outputting an electromotive force from the electromotive force cell, and another one of the pair of electrodes is an exhaust side electrode, which becomes a negative side at the time of outputting the electromotive force from the electromotive force cell;
the current conduction regulating device induces the flow of the predetermined constant electric current, which has a current value that is required to shift an equilibrium point of a gas reaction around the exhaust side electrode of the electromotive force cell to the second air-to-fuel ratio point or an adjacent point that is adjacent to the second air-to-fuel ratio point.

7. The gas sensor control device according to claim 6, wherein the current conduction regulating device induces the flow of the predetermined constant electric current, which has the current value that is required to shift the equilibrium point of the gas reaction around the exhaust side electrode of the electromotive force cell to a point on a rich side of the second air-to-fuel ratio point.

* * * * *